US011123509B2

(12) United States Patent
Purdy

(10) Patent No.: US 11,123,509 B2
(45) Date of Patent: Sep. 21, 2021

(54) RESPIRATORY TREATMENT APPARATUS

(71) Applicant: PROVINCIAL HEALTH SERVICES AUTHORITY, Vancouver (CA)

(72) Inventor: F. Robert Purdy, Vancouver (CA)

(73) Assignee: Provincial Health Services Authority, Vancouver (CA)

( * ) Notice: Subject to any disclaimer, the term of this patent is extended or adjusted under 35 U.S.C. 154(b) by 738 days.

(21) Appl. No.: 15/594,381

(22) Filed: May 12, 2017

(65) Prior Publication Data
US 2018/0326168 A1   Nov. 15, 2018

(51) Int. Cl.
*A61M 16/04* (2006.01)
*A61F 2/50* (2006.01)

(52) U.S. Cl.
CPC .......... *A61M 16/0404* (2014.02); *A61F 2/50* (2013.01); *A61M 16/044* (2013.01); *A61M 16/0459* (2014.02); *A61M 16/0463* (2013.01)

(58) Field of Classification Search
CPC ... A61F 2/50; A61M 16/0404; A61M 16/044; A61M 16/0459; A61M 16/0463;
(Continued)

(56) References Cited

U.S. PATENT DOCUMENTS 3,964,488 A *   6/1976   Ring ..................... A61M 16/04
                                                    128/207.14
4,840,172 A     6/1989   Augustine et al.
(Continued)

FOREIGN PATENT DOCUMENTS

CA   1181311     1/1985
CA   2116697     12/1993
(Continued)

OTHER PUBLICATIONS

Templeton et al., "Bending the rules: a novel approach to placement and retrospective experience with the 5 French Arndt endobronchial blocker in children <2 years," Pediatric Anesthesia 26 (2016) 512-520.
(Continued)

*Primary Examiner* — Margaret M Luarca
*Assistant Examiner* — Ned T Heffner
(74) *Attorney, Agent, or Firm* — Oyen Wiggs Green & Mutala LLP

(57) ABSTRACT

Disclosed is a respiratory treatment apparatus that may be especially helpful for pediatric patients, though it may be useful for patients of all ages. In one embodiment, the apparatus comprises an endotracheal tube that is physically coupled to a bronchial blocker in a non-concentric fashion. In another embodiment, the apparatus comprises an endotracheal tube that is physically coupled to a steering balloon apparatus. The endotracheal tube, bronchial blocker, and/or steering balloon apparatus may be non-unitary components that are attachable to one another with one or more attachment structures, and once physically coupled, may be put to use. The endotracheal tube and bronchial blocker and steering balloon apparatus may be selected from a plurality of endotracheal tubes and bronchial blockers and steering balloon apparatus, to create an assembled apparatus that meets the needs of the patient.

19 Claims, 7 Drawing Sheets

(58) Field of Classification Search
CPC .... A61M 16/00; A61M 16/04; A61M 16/046; A61M 25/00; A61M 25/10; A61M 25/1002–1009
See application file for complete search history.

(56) References Cited

U.S. PATENT DOCUMENTS

| | | | |
|---|---|---|---|
| 5,315,992 A | 5/1994 | Dalton | |
| 5,588,424 A | 12/1996 | Insler et al. | |
| 5,904,648 A | 5/1999 | Arndt et al. | |
| 5,954,636 A | 9/1999 | Schwartz et al. | |
| 6,443,156 B1 * | 9/2002 | Niklason | A61M 16/04 128/207.14 |
| 6,609,521 B1 | 8/2003 | Belani et al. | |
| 7,775,968 B2 | 8/2010 | Mathis | |
| 7,900,634 B2 | 3/2011 | Tjong | |
| 8,375,952 B2 | 2/2013 | Miller et al. | |
| 8,555,887 B2 | 10/2013 | Lisogurski | |
| 8,887,730 B2 | 11/2014 | Wood et al. | |
| 8,968,511 B2 | 3/2015 | Macan et al. | |
| 9,125,639 B2 | 9/2015 | Mathis et al. | |
| 9,132,212 B2 | 9/2015 | Clayton | |
| 9,314,580 B2 | 4/2016 | Hammer | |
| 9,427,142 B2 | 8/2016 | Terliuc | |
| 9,526,856 B2 | 12/2016 | Azagury et al. | |
| 9,687,621 B2 | 6/2017 | Hoftman | |
| 2002/0147462 A1 | 10/2002 | Mair et al. | |
| 2004/0144387 A1 | 7/2004 | Amar | |
| 2006/0090761 A1 | 5/2006 | Kurrus | |
| 2007/0043350 A1 | 2/2007 | Soltesz et al. | |
| 2008/0035154 A1 * | 2/2008 | Johnson | A61M 16/04 128/207.14 |
| 2009/0260625 A1 * | 10/2009 | Wondka | A61M 16/04 128/203.12 |
| 2010/0249639 A1 * | 9/2010 | Bhatt | A61B 1/00082 600/546 |
| 2011/0015613 A1 | 1/2011 | Anzai | |
| 2012/0302833 A1 * | 11/2012 | Hayman | A61B 5/061 600/120 |
| 2013/0186407 A1 | 7/2013 | Hammer | |
| 2016/0243326 A1 * | 8/2016 | Hammer | A61M 16/0404 |
| 2016/0256646 A1 | 9/2016 | Vazales | |
| 2016/0256650 A1 * | 9/2016 | Wang | A61M 16/0481 |
| 2017/0072154 A1 * | 3/2017 | Hoftman | A61M 16/0816 |

FOREIGN PATENT DOCUMENTS

| | | |
|---|---|---|
| CA | 2309044 | 5/1998 |
| CA | 2324288 | 9/1999 |
| CA | 2485340 | 8/2004 |
| CA | 2895488 | 8/2004 |
| CA | 2566259 | 12/2005 |
| CA | 2610933 | 12/2006 |
| CA | 2793853 | 9/2011 |
| CA | 2841704 | 1/2013 |
| CA | 2816129 | 11/2013 |
| CA | 2893048 | 6/2015 |
| WO | 2009070970 | 6/2009 |
| WO | 2013188845 | 11/2013 |

OTHER PUBLICATIONS

Pawar et al., "One lung ventilation in infants and children: experience with Marraro double lumen tube," Pediatric Anesthesia 2005 15:204-208.

Fitzgerald et al., "Techniques for single lung ventilation in infants and children," ATOTW 322 (Oct. 23, 2015), www.wfsahq.org/resources/anaesthesia-tutorial-of-the-week.

Wilson et al., "Anesthetic techniques to facilitate lung lavage for pulmonary alveolar proteinosis in children—new airway techniques and a review of the literature," Pediatric Anesthesia 25 (2015) 546-553.

Golianu, et al., "Pediatric thoracic anesthesia," Curr Opin Anaesthesiol. Feb. 2005;18(1):5-11.

* cited by examiner

RESPIRATORY TREATMENT APPARATUS

FIELD

The present disclosure is directed to apparatus used for medical treatment involving the respiratory system, and more particularly, apparatus for occluding a part of the respiratory system or isolating the respiratory system from other systems such as the digestive system.

BACKGROUND

In a healthy patient, both lungs inflate and deflate together during respiration. In cases of some pulmonary or thoracic surgeries, it may be important to isolate a lung or mechanically separate the lungs from working together. With "lung isolation" and/or "one lung ventilation," one lung participates in respiration, while the other lung may be deflated or rendered inactive. Lung isolation and/or one lung ventilation may be used in cases such as those in which one lung is healthy and the other is not, or when surgery is required on one side of the chest, or in numerous other situations.

To achieve lung isolation and/or one lung ventilation, a portion of the respiratory system may be intentionally occluded by medical apparatus. Typically an anatomical passage to a lung or a portion of a lung may be blocked to prevent the flow of fluids (gases and/or liquids). Such an occlusion may prevent substances such as blood and secretions from moving from one lung to the other lung, for example. It allows the blocked side to collapse or deflate and improve access for surgery.

Lung isolation and/or one lung ventilation in pediatric patients (most notably the very small patients: premature babies, neonates, and infants) may present challenges that are not present in adult human beings. Some of the challenges are due in part to the comparatively small size of the anatomical structures of pediatric patients, notably the trachea and the two major bronchi.

Also, it is not uncommon for newborns to have a congenital malformation of the respiratory system called a Tracheoesophageal Fistulas (or TEF). With a TEF, there may be a direct connection between the trachea of the respiratory system and the esophagus of the digestive system. TEFs are often associated with several other congenital malformations, including cardiac defects. The connection between the esophagus and trachea may allow stomach contents to regurgitate into the trachea and lungs. When a baby having a TEF is resuscitated or anesthetized, positive pressure ventilation may severely inflate the stomach, potentially compromising ventilation and potentially leading to life-threatening consequences.

DETAILED DESCRIPTION

The present disclosure describes apparatus for medical treatment involving the respiratory system. Such medical treatment may include lung isolation and/or one lung ventilation, and procedures to address physiological concerns or malformations such as TEFs. The disclosure will be presented, at least in part, in the context of use with pediatric patients, for whom the disclosed apparatus may carry many potential advantages. It should be noted, however, that the disclosed apparatus is not limited to use with pediatric patients, and one potential advantage of this disclosure is that the apparatus may be readily scaled or adapted for use with adult patients. (The apparatus may be adapted for veterinary patients as well, but this disclosure will focus upon human patients.) Also, many of the potential advantages of the apparatus carry over for patients of all ages. For example, the apparatus may be useful for children and adults in emergency and intensive care settings, where rapid lung isolation is required, such as in the case of a massive pulmonary hemorrhage. Further potential benefits will be discussed below.

Figure 1:
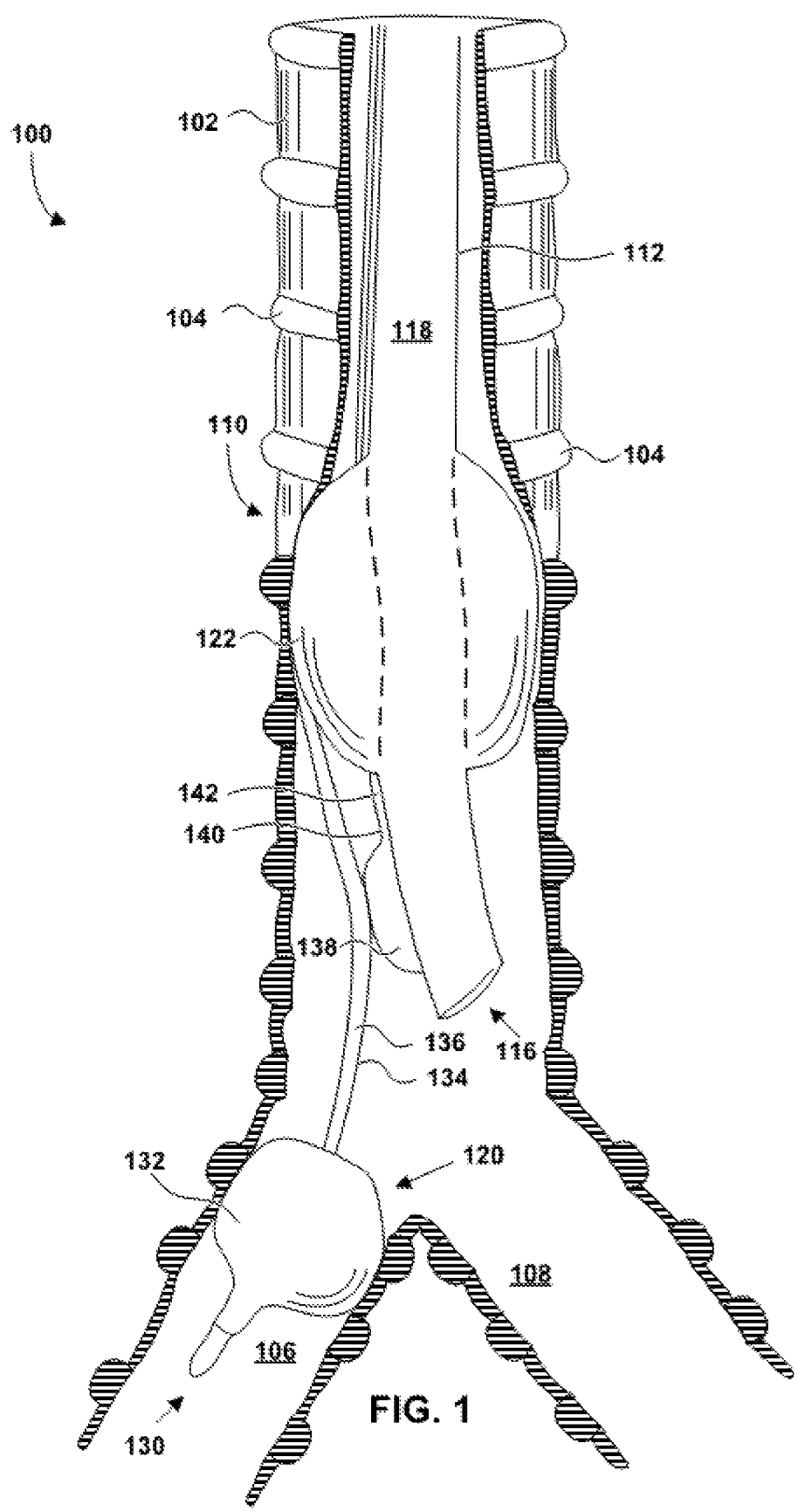
FIG. 1 is a schematic view of an illustrative medical device in a human respiratory system.

FIG. 1 is an illustration of a portion of a human respiratory system 100. For purposes of illustration, the portion of the human respiratory system 100 may be that of an older pediatric patient (rather than an infant or neonate) having anatomical passages similar to but substantially smaller than comparable structures on an adult.

The portion of the human respiratory system 100 includes a trachea 102, having cartilaginous rings 104. The trachea 102 serves as an airway between the environment and the patient's lungs (not shown). The airway of the trachea 102 branches at the carina into a right mainstem bronchus 106 and a left mainstem bronchus 108. (By convention, left and right are from the point of view of the patient.) The right bronchus 106 enters the right lung (not shown) and the left bronchus 108 enters the left lung (not shown). The airways of the mainstem bronchi 106, 108 divide into smaller airway passages called secondary bronchi (not shown) and the secondary bronchi divide into tertiary bronchi (not shown). Occluding the mainstem bronchus 106 or 108 of a lung will isolate all of the airway passages of that lung, and the non-occluded bronchus 108 or 106 remains open, allowing ventilation through that bronchus.

In most patients, there are some anatomical differences between the right side and the left side of the respiratory system. These anatomical differences are not depicted in FIG. 1.

Figure 2:
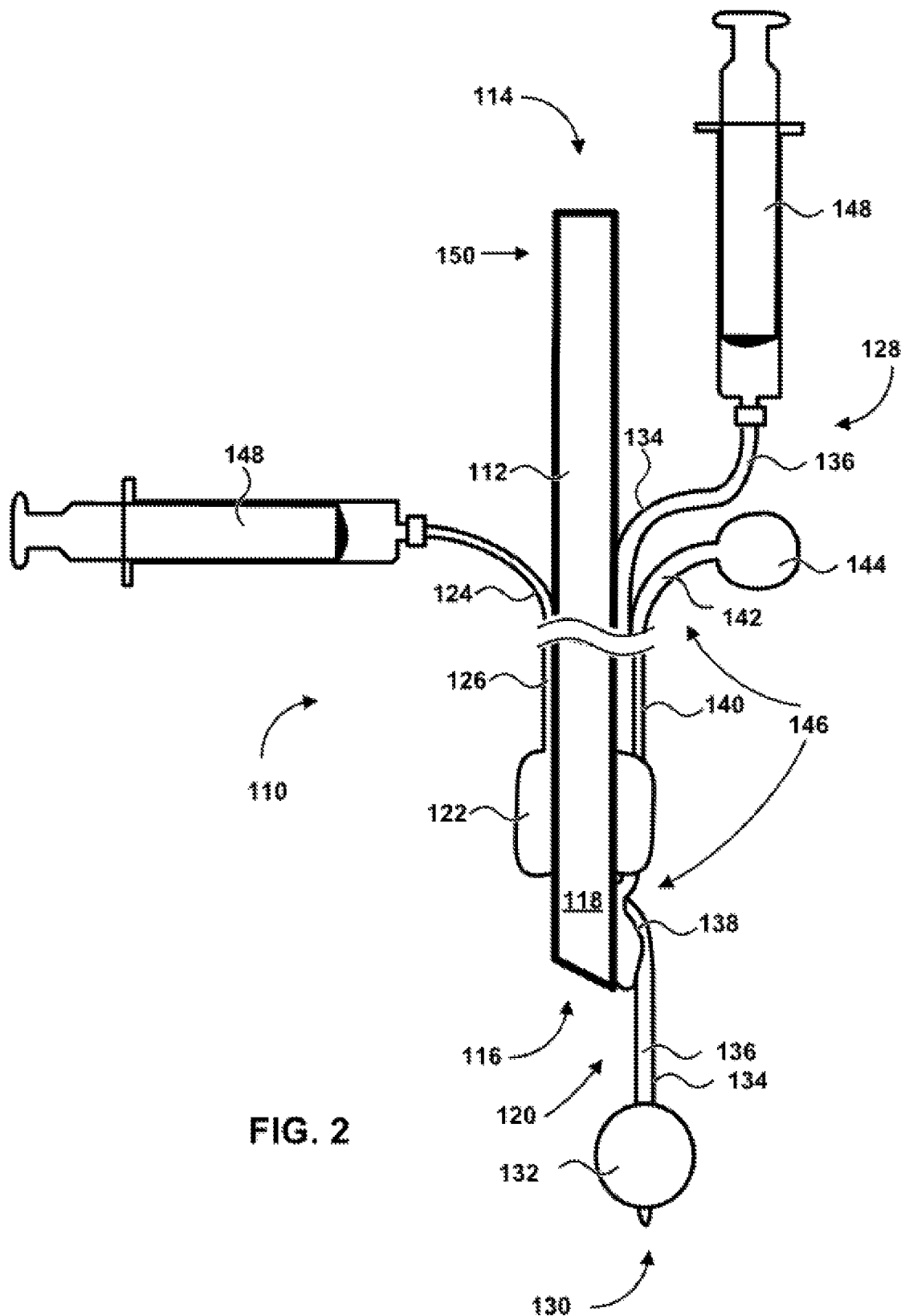
FIG. 2 is a schematic view of the illustrative medical device in shown in FIG. 1, illustrating the constituent components thereof.

FIG. 1 depicts an illustrative apparatus 110, deployed to achieve lung isolation and/or one lung ventilation. FIG. 2 is a schematic diagram that shows the apparatus 110 in a manner that depicts the components of the apparatus 110 for clarity; but the components are not drawn to scale, and not all structures are depicted in both FIG. 1 and FIG. 2.

The apparatus 110 includes an endotracheal tube 112 inserted into the trachea 102. The endotracheal tube 112 generally serves the purposes of establishing, maintaining and securing the airway, and avoiding interference from anatomical structures such as the vocal chords or epiglottis. The endotracheal tube has a proximal end 114 and a distal end 116. The distal end 116 is typically beveled and may but need not include a "Murphy Eye" (not shown in FIG. 1). The distal end 116 is inserted into the patient's trachea 102. The endotracheal tube 112 includes an endotracheal tube lumen 118 through which some solids and fluids and medical instruments may pass. In some surgical procedures, the endotracheal tube 112 forms a passageway for introduction of medical apparatus, such as a bronchial blocker (also called an endobronchial blocker), through the endotracheal tube lumen 118 into the patient's respiratory system 100. In FIG. 1, however, a bronchial blocker 120 is introduced into the patient's respiratory system 100, but not by way of passage through the endotracheal tube lumen 118.

The endotracheal tube 112 may be described in terms of its external diameter, from one cross-sectional edge to another. The endotracheal tube 112 may also be described in terms of its internal diameter, basically the width of the endotracheal tube lumen 118. Such dimensions are typically expressed as conventional dimensions with some degree of tolerance, and not as exact measurements.

The endotracheal tube 110 may include an inflatable element 122 (which may be denoted for convenience as a "first" inflatable element 122), shown in the form of a circumferential inflatable cuff (and an element of this kind is often referred to as a "cuff"). For a very small patient, the cuff 122 may be considerably smaller than is depicted in FIG. 1, and may, for some pediatric patients, be omitted. (If the cuff is omitted, the endotracheal tube is termed an "uncuffed" endotracheal tube.) In FIG. 1, the cuff 122 is depicted in its inflated configuration, and in FIG. 2, the cuff 122 is less than completely inflated. The endotracheal tube 112 typically includes an inflation tube 124 having an inflation lumen 126 (not shown in FIG. 1, and which may be denoted for convenience as a "first" inflation tube 124 having a "first" inflation lumen 126, distinct from the endotracheal tube 112 and endotracheal tube lumen 118), to supply inflation to the cuff 122 or deflate the cuff 122. The first inflation tube 124 with the first inflation lumen 126 is in fluid communication with the first inflatable element 122. An inflation fluid such as air passing through the first inflation lumen 126 will inflate or deflate the cuff 122, depending upon whether the inflation fluid is moving toward the proximal end 114 or the distal end 116.

The cuff 122 shown in FIG. 1 is disposed near to the distal end 116 of the endotracheal tube 112, though typically a small distance away from the distal end 116. The distal end 116 of the endotracheal tube 112 may extend into the trachea 102 beyond the cuff 122. The cuff 122 shown in FIG. 1 is a low pressure-high volume type cuff, which when inflated contacts a relatively large surface area of the inner walls of the trachea 102. Further, the cuff 122 shown in FIG. 1 is of a substantially uniform cross-section, contacting the walls of the trachea 102 substantially equally in all directions. The cuff 122 shown is illustrative, and the present disclosure is not limited to a particular configuration of cuff, nor is the disclosure limited to a cuff-like first inflatable element 122. When inflated, the cuff 122 makes a low-pressure seal with the trachea 102. This seal, among other things, facilitates positive pressure ventilation and protects the lungs from soiling from above, such as soiling with oral secretions or stomach content. As will be discussed below, the cuff 122 may serve additional functions as well, and may be configured to perform some functions effectively.

FIG. 1 further shows a bronchial blocker 120. The bronchial blocker 120 includes a proximal end 128 and a distal end 130. The distal end 130 of the bronchial blocker 120 may also be called the "blocker tip." The distal end 130 of the bronchial blocker 120 is deployed through the trachea 102 of the patient and into a mainstem bronchus 106 or 108. FIG. 1 depicts the distal end 130 of the bronchial blocker 120 descending into the right bronchus 106 (though descent into the left bronchus 108 may also be achieved, as described below). The bronchial blocker 120 includes an inflatable element 132 (which may be denoted for convenience as a "second" inflatable element) 132 and an inflation tube 134 having an inflation lumen 136 (which may be denoted for convenience as a "second" inflation tube 134 having a "second" inflation lumen 136) that is in fluid communication with the second inflatable element 132. An inflation fluid such as air passing through the second inflation lumen 136 of the second inflation tube 134 toward the distal end 130 will inflate the second inflatable element 132. Similarly, an inflation fluid may move through the second inflation lumen 136 of the second inflation tube 134 toward the proximal end 128, causing the second inflatable element 132 to deflate. The second inflatable element 132 may conventionally be referred to as a "balloon," which is disposed near to the distal end 130 of the bronchial blocker 120. When inflated, the second inflatable element 132 occludes the bronchus 106 or 108 and thereby isolates the lung.

As shown in FIG. 1, the bronchial blocker 120 is not deployed through the endotracheal tube lumen 118. In other words, the second inflation tube 134 (and its lumen 136) of the bronchial blocker 120 and the endotracheal tube 112 (and its lumen 118) are non-concentric, that is, the former is not inside the latter. Rather, the second inflation tube 134 of the bronchial blocker 120 and the endotracheal tube 112 are adjacent or side-by-side.

As depicted in FIG. 1, the endotracheal tube 112 includes another inflatable element 138 (which may be denoted for convenience as a "third" inflatable element 138) and an inflation tube 140 having an inflation lumen 142 (which may be denoted for convenience as a "third" inflation tube 140 having a "third" inflation lumen 142) that serves to supply inflation to the third inflatable element 138 or deflate the third inflatable element 138. The third inflatable element 138 is disposed near to the distal end 130 of the endotracheal tube 112, and is generally nearer to the distal end 116 of the endotracheal tube 112 than is the first inflatable element 122. The third inflatable element 138 may be referred to conventionally as a "balloon," though the third inflatable element 138 may be structurally different from the second inflatable element 132 (and may also be structurally different from the first inflatable element 122). All inflatable elements 122, 132, and 138 may be inflated and/or deflated independently. The third inflatable element 138 serves as a steering or directional or deflecting element, that may urge the distal end 130 of the bronchial blocker 120 into the right mainstem bronchus 106 or the left mainstem bronchus 108, as desired. In FIGS. 1 and 2, the third inflatable element 138 is depicted as deflated. Further, in FIGS. 1 and 2, the third inflatable element 138 is non-circumferential (not a circumferential element surrounding most or all of the endotracheal tube 112), dissimilar from the depicted first inflatable element 122; the third inflatable element 138 is also dissimilar from the second inflatable element 132 which is an omnidirectional or uniformly expanding balloon. Rather, the third inflatable element 138 may be small in comparison to the first inflatable element 122 and the second inflatable element 132, and may be configured to expand directionally or laterally away from the third inflation tube 140, and/or laterally away from the lumen 118 of the endotracheal tube 112. In other words, the third inflatable element 138 may be configured to expand laterally away from a side of the distal end 116 of the endotracheal tube 112.

In practice, the third inflatable element 138 may be thought of as a "steering balloon," used to deflect or steer the blocker tip 130 to the lung that is to be occluded. As the distal end 130 of the bronchial blocker 120 is inserted through the trachea 102, and the distal end 130 is near to the right mainstem 106 bronchus and the left mainstem bronchus 108, the third inflatable element 138 may be inflated, thereby deflecting or biasing the blocker tip 130 toward the desired bronchus. In FIG. 1, the third inflatable element 138 is shown deployed so as to bear against second inflation tube 134 of the bronchial blocker 120 (the third inflatable element 138 shown as now deflated), and thereby steer the blocker tip 130. The third inflatable element 138 may be deployed in other ways as well, and may steer the blocker tip 130 without necessarily bearing against the bronchial blocker 120. The third inflatable element 138 would generally not be inflated to a degree to block any anatomical passageway or to hold any apparatus in place; and once the desired deflection is achieved and the distal end 130 of the bronchial blocker 120 is entering the correct bronchus, the third inflatable element 138 may be deflated. Such practice may enable fine control over the manipulation of the blocker tip 130 toward the correct site. Fine control over the manipulation of the blocker tip 130 may also facilitate endotracheal intubation, notably during passage of the apparatus 110 through the larynx of the patient during endotracheal intubation.

In one variation, the third inflatable element 138 may be inflated by use of a bulb or low-pressure balloon 144 near the proximal end 128 of the endotracheal tube 112. The third inflatable element 138 would be, by contrast, a high-pressure balloon. Thus, the third inflatable element 138 would be biased to be deflated, while the bulb 144 would tend to be expanded. The bulb 144 and third inflatable element 138 would be in fluid communication with one another via the third inflation lumen 142. The bulb 144, third lumen 142, third inflation tube 140, and third inflatable element 138 could be a closed system. Such a system may be one example of a steering balloon apparatus 146. Following insertion of the bronchial blocker 120 through the trachea 102, the medical professional (typically the anesthesiologist, who is usually responsible for placement of apparatus into the patient's respiratory system 100) may manually apply pressure to the bulb 144, thereby expelling air from the bulb 144 through the third inflation lumen, thereby expanding the third inflatable element 138, thereby steering the blocker tip 130. After the blocker tip 130 is steered where it should go, the medical professional may release pressure on the bulb 144, and the air in the third inflatable element 138 would move through the lumen 142 to the low-pressure bulb 144, thereby deflating the third inflatable element 138.

Inflatable elements may be inflated or deflated by mechanical elements 148 such as a syringe with a plunger such that, when the syringe plunger is depressed, air is forced out of the syringe and down a lumen and into the inflatable element. The inflatable element may be maintained in an inflated condition by maintaining the plunger in a depressed state. The inflatable element can be deflated by withdrawal of the syringe plunger from the depressed state. In the case of the third inflatable element 138, inflation is expected to be for a comparative small interval of time, and the third inflatable element 138 is ordinarily not maintained in an inflated condition for a long time. Use of a bulb 144 such as described above may therefore be a more efficient apparatus for inflation and deflation. The concept includes other mechanical elements 148 for inflation and deflation, however.

In practice, a typical use of the apparatus 110 would be as follows. The endotracheal tube 112 and bronchial blocker 120 would typically be "attachable" to one another. That is, the endotracheal tube 112 and bronchial blocker 120 may be, prior to the patient's surgical procedure, separate and non-unitary elements (that is, the endotracheal tube 112 and bronchial blocker 120 need not be, but may be, a unitary apparatus for which attachment is unnecessary). The endotracheal tube 112 and bronchial blocker 120 would, however, be sized and configured to be physically coupled to one another to form the assembled apparatus 110. Further, the endotracheal tube 112 and bronchial blocker 120 may be configured to be capable of physical coupling to one another with an attachment structure. Some attachment structures are described or illustrated below. Generally speaking, the endotracheal tube 112 and bronchial blocker 120 are consistently oriented, so that the proximal end 114 of the endotracheal tube 112 is near the proximal end 128 of the bronchial blocker 120, and the distal end 116 of the endotracheal tube 112 is near the distal end 130 of the bronchial blocker 120. If a steering balloon is desired, then a third inflatable element 138, third tube 140 with third lumen 142, and bulb 144 may also be physically coupled to the endotracheal tube 112, the bronchial blocker 120, or both. In FIG. 1, the third inflatable element 138 is depicted as physically coupled to endotracheal tube 112 near the distal end 116 of the endotracheal tube 112.

The assembled apparatus 110, comprising an endotracheal tube 112, bronchial blocker 120 (with second inflatable element 132 and third inflatable element 138 and associated apparatus) are simultaneously introduced into the trachea 102. As will be discussed below, the endotracheal tube 112 and bronchial blocker 120 may be physically coupled so that they can be inserted into the patient as a single unit. When the distal end 130 of the bronchial blocker 120 reaches the mainstem bronchi 106 and 108, the third inflatable element 138 may be briefly inflated to steer or defect the distal end 130 of the bronchial blocker 120 into the correct bronchus. Once the distal end 130 is steered into the correct bronchus, the endotracheal tube 112 and bronchial blocker 120 may be inserted farther into the trachea 102. The distal end 116 of the endotracheal tube 112 ordinarily would not be inserted into either the right bronchus 106 or the left bronchus 108, but would remain in the trachea 102. Medical instrumentation, such as a fiber optic bronchoscope (not shown), may be used to check positioning of the endotracheal tube 112 and bronchial blocker 120. Such instrumentation may be introduced through a port 150 on the proximal end 114 of the endotracheal tube 112. When positioning seems to be satisfactory, the cuff 122 may be inflated to hold the apparatus 110 in a fixed position with respect to the trachea 102, and the second inflatable element 138 may be inflated to occlude the correct mainstem bronchus 106 or 108.

FIG. 1 shows the bronchial blocker 120 steered to the right bronchus 106. The bronchial blocker 120 may also be steered to the left bronchus 108. As will be discussed in more detail below, the bronchial blocker 120 may be physically coupled to the endotracheal tube 112 in one fashion for positioning in the right bronchus 106, and in a different fashion for positioning in the left bronchus 108. When the right bronchus 106 is to be occluded, the bronchial blocker 120 may be physically coupled or attached to the right side of the endotracheal tube 112; and when the left bronchus 108 is to be blocked, the bronchial blocker 120 is physically coupled or attached to the left side of the endotracheal tube 112.

The use of a steering balloon apparatus 146 is optional. In another embodiment, the third inflatable element 138 and the third inflation tube 140 having the third inflation lumen 142, and the bulb 144 are omitted. The bronchial blocker 120 may be a conventional bronchial blocker. In practice, the assembled apparatus 110 comprising an endotracheal tube 112 and bronchial blocker 120 are simultaneously introduced into the trachea 102. When the distal end 130 of the bronchial blocker 120 reaches the mainstem bronchi 106 and 108, the first inflatable element 122 may be gently, but generally not fully, inflated. This maneuver may serve to deflect the distal end 130 of the bronchial blocker 120 into the correct bronchus. (Some variations of cuffs may tend to bias the distal end 130 of the bronchial blocker 120 to the left, other variations to the right.) Once the distal element 130 is steered into the correct bronchus, the first inflatable element 122 may be deflated, the endotracheal tube 112 and bronchial blocker 120 may be positioned, and the first inflatable element 122 may be re-inflated, and the second inflatable element 132 may be inflated to occlude the correct mainstem bronchus.

In a further variation, the bronchial blocker 120 is optional. In this variation, the third inflation tube 140 may be physically coupled to the endotracheal tube 112. In this variation, the third inflatable element 138 of the steering balloon apparatus 146 may be used to steer apparatus other than a bronchial blocker. For purposes of illustration, a catheter (or other medical instrument, such as, but not limited to, a flexible biopsy forceps, a grasping forceps or basket for foreign bodies, a cautery cable, or a laser) may be steered to a correct lung with the assistance of the third inflatable element 138. A catheter directed into the respiratory system 100 through the endotracheal tube 112 may have, for example, a wire (or thread or suture; the word "wire" will be used to encompass all variations of thin, elongated, generally flexible or directionally changeable elements) attached to the catheter tip. When placed in tension, the wire may tend to deflect the tip of the catheter. The deflection may move the catheter tip medially (that is, bow the catheter so that the tip is directed toward the body midline), but the desire may be to move the body of the catheter laterally (away from the midline). In such a case, the third inflatable element 138 may be inflated to steer the catheter laterally, while the catheter tip may be pointed in another direction. In other words, instrument steering may be accomplished with the third inflatable element 138 alone or acting in concert with another steering element. In addition to manipulating the wire, the direction in which the catheter tip is pointing may also be steered by twisting or rotating the endotracheal tube 112. Steering with multiple steering elements may support fine control and precise positioning of the instrument.

Fine control and positioning may be very useful when dealing with a TEF. On occasion, placement of a wire, catheter, balloon catheter (which may serve as a blocker), or other instrument through the trachea and into the fistula may be required to facilitate anesthesia, to protect the lungs from soiling, and to aid the surgeons in identifying the fistula and surgically correcting it. Placement of this wire, catheter or balloon catheter can be challenging. Use of one or more steering techniques and apparatus, as described above and below, may advantageous assist in steering an instrument (such as a bronchial blocker, wire, catheter or balloon catheter) towards the TEF. This will be discussed in more detail below.

In a further variation, a steering balloon apparatus 146 and another piece of apparatus or instrument may be physically coupled to the endotracheal tube 112. For example, the catheter described in the previous paragraph (or another kind of instrument) may be physically coupled to the endotracheal tube 112 (instead of going through the endotracheal tube 112). The wire may be inside the endotracheal tube 112, or outside the endotracheal tube 112, or partway inside and outside (e.g., passing through a "Murphy Eye" near the distal end 116 of the endotracheal tube 112). In this variation, the wire and the third inflatable element 138 may cooperate to steer the catheter tip.

It is also contemplated that the bronchial blocker 120 (or other instrument) may be steered by multiple steering elements as well, including applying tension to a wire (not shown), rotating the endotracheal tube 112, deflecting with the inflatable element 138, and inflating or deflating the cuff 122.

In a typical implementation involving an endotracheal tube 112 and bronchial blocker 120, the endotracheal tube 112 and bronchial blocker 120 are physically coupled to one another so that they are inserted into the patient as a single unit. That is, it is unnecessary to insert the endotracheal tube 112, and insert the bronchial blocker 120 separately. Components are "physically coupled" when they are attached or connected or joined to one another, in any fashion, whether releasably or substantially permanently, so that physical activity of one component generally affects the other. The physical attachment or coupling may be direct or by way of one or more intermediate elements. Physical coupling does not require attachment along a full length of a device or at any set number of attachment sites.

The endotracheal tube 112 and bronchial blocker 120 (and/or wire, and/or catheter, and/or any other instrument) may be physically coupled to one another in a number of ways, such as the following. First: the bronchial blocker 120 may be fixed by a bio-compatible adhesive (such as a glue) to a side of the endotracheal tube 112. The adhesive may be applied at any time. Second: the endotracheal tube 112 may be constructed to include a small groove or slot down the side of the endotracheal tube 112. This small groove would be sized to receive the bronchial blocker 120 (or any part thereof, such as second inflation tube 134, or any other instrument). The fit may be sufficiently snug that there would be a friction fit (no adhesive necessary) so that the second inflation tube 134 would not readily disengage from the groove on the side of the endotracheal tube 112. Third: the small groove may include an adhesive, such as a self-adhesive strip, such that the bronchial blocker 120 (or any part thereof, or any other instrument) would be held in the groove in part by adhesion. The adhesive strip may be protected by a backing that can be peeled away to expose a bio-compatible adhesive. Apart from a groove, the endotracheal tube 112 and/or the bronchial blocker 120 (or any part thereof, or any other instrument) may include other physical features (such as flat surfaces or visible guidelines) to aid in adhesion. Fourth: a self-adhesive strip may be in place down the side of the endotracheal tube 112, without a groove or other physical feature. The bronchial blocker 120 (or any part thereof, or any other instrument) blocker 120 would attach to the endotracheal tube 112 by adhesion. Fifth: small structures and/or mechanical fasteners may be deployed down a side of the endotracheal tube 112 and/or the bronchial blocker 120 (or any part thereof, or any other instrument) that can mechanically fasten the components or instruments to the endotracheal tube 112. An example of such structures and/or fasteners may be small clips on a side of the endotracheal tube 112, into which the components or instruments may be pressed. Other mechanical fasteners, such as snaps, catches, loops, and hooks, are also contemplated. Sixth: the endotracheal tube 112 and the bronchial blocker 120 (or any part thereof, or any other instrument) may be constructed as a unitary structure, rather than as separate structures to be joined. In this way, a wall of the endotracheal tube 112 may serve also as the second tube 134, for example, and may accommodate the second lumen 136. This list of ways to physically couple the endotracheal tube 112 and bronchial blocker 120 is not an exclusive list, and any combination of ways may be employed.

The structures by which the endotracheal tube 112 and bronchial blocker 120 may be physically coupled to one and another (especially the first five examples, and other similar structures) may be individually or collectively described as "attachment structures." Such attachment structures may be a component of the endotracheal tube 112 (such as one or more grooves or clefts), or of the bronchial blocker 120 (such as a single adhesive strip), or both (such as cooperative structures on both devices), or neither (such as a separate adhesive that is applied to physically couple the endotracheal tube 112 and the bronchial blocker 120).

It has been discovered that physically coupling the endotracheal tube 112 and bronchial blocker 120 to one another need not adversely affect the operation of the first inflatable element 122. The second inflation tube 134 of the bronchial blocker 120 has been found not to significantly affect the seal created when a cuff 122 is inflated. Although the first inflatable element 122 may include one or more structures (such as a groove) to accommodate the second inflation tube 134, experience has indicated that such accommodating structures may be unnecessary. Also, experience has indicated that inflation of a low-pressure first inflatable element 122 does not significantly affect the operation of the bronchial blocker 120 or the capability of inflating or deflating the second inflatable element 132.

Figure 3A:
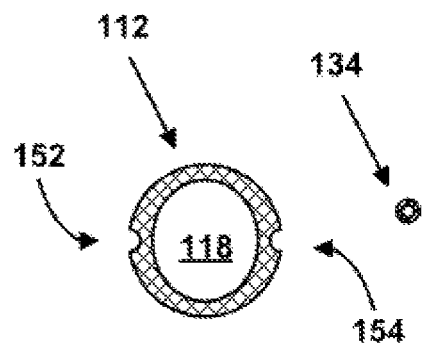
FIG. 3A is a cross-sectional view of an illustrative endotracheal tube and a tube of a bronchial blocker.
Figure 3B:
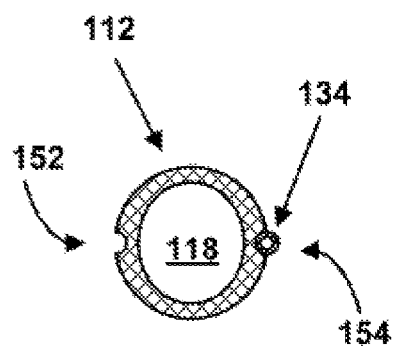
FIG. 3B is a cross-sectional view of the illustrative endotracheal tube and the tube of the bronchial blocker depicted in FIG. 3A, with the endotracheal tube physically coupled to the tube of the bronchial blocker.
Figure 3C:
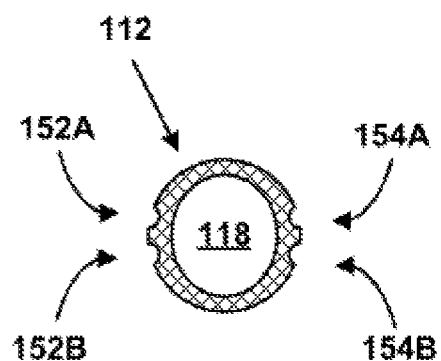
FIG. 3C is a cross-sectional view of another illustrative endotracheal tube.

It may be noted that the attachment structures may be disposed on multiple places on the endotracheal tube 112. Further, some attachment structures may be used, and some may be unused. Illustrations of this concept are shown in FIGS. 3A, 3B, and 3C. By way of example, an endotracheal tube 112, shown in cross-section, may have a first groove 152 disposed on one side, and a second groove 154 disposed on an opposite side. The first groove 152 and the second groove 154 are sized to receive the second inflation tube 134 that is a component of the bronchial blocker 120 (or other instrument). The second tube 134 of the bronchial blocker 120 may be physically coupled to the endotracheal tube 112 using either groove 152 or 154. In FIG. 3B, the second tube 134 is physically coupled in the second groove 154, and the first groove 152 is unused. The selection of first groove 152 or second groove 154 may bias the bronchial blocker 120 to tend toward the right bronchus 106 or the left bronchus 108. Such biasing may assist in steering the blocker tip 130 to the correct bronchus. The grooves need not be disposed as shown in FIGS. 3A and 3B, and there need not be any particular number of grooves. FIG. 3C illustrates one possible variation, with a set of two first grooves 152A and 152B disposed on one side, and a set of two second grooves 154A and 154B disposed on the opposite side. As an example, one groove on a side may accommodate a bronchial blocker 120, and the other groove on the same side may accommodate a steering balloon apparatus 146.

In the above list, many of the techniques (the first five examples) support physically coupling the attachable endotracheal tube 112 and attachable bronchial blocker 120 shortly before actual use. Consequently, an endotracheal tube 112 may be selected, sized and/or configured for the needs of the patient, and a bronchial blocker 120 may be selected, according to the patient's needs, and the selected endotracheal tube 112 and selected bronchial blocker 120 may be physically coupled together. Also, selection of which side of the endotracheal tube 112 for physical coupling of the bronchial blocker 120 may support ready assembly of an apparatus 110 most useful for the patient, according to factors such as which lung is the correct lung to be occluded, or the patient's size. Physical coupling may support customization to a variety of patients in other ways as well. Such physical coupling may take only a matter of seconds or minutes to accomplish. The endotracheal tube 112, or the bronchial blocker 120, or steering balloon apparatus 146, or all three, may include physical features such as markings that may assist the person physically coupling the components to physically couple them in a desirable way (such as physically coupling them so that the blocker tip 130 extends a desired length beyond the distal end 116 of the endotracheal tube 112), which may make physical coupling proceed more quickly. As a further consideration, the technique for physically coupling the components may be different depending upon the age or size of the patient. For a very small patient, the third technique (groove plus adhesive) may be the most practical, but for a larger patient, a different technique may be more practical.

The apparatus as described may be readily sized for pediatric patients of a range of ages, as well as adult patients. The size range of the endotracheal tube 112 may be from 2.0 to 9.0 mm internal diameter (that is, the size range may be small for premature babies and larger for adults ranging in size from 500 grams up to 300 kg or more for adults). Physically coupling the endotracheal tube 112 and bronchial blocker 120 need not markedly change either the external diameter or the internal diameter of the endotracheal tube 112. Once the endotracheal tube 112 and bronchial blocker 120 are physically coupled, the apparatus may be inserted into the trachea 102. The bronchial blocker 120 may be quickly, easily, precisely and safely positioned into the right bronchus 106 or the left bronchus 108, under direct vision such as by viewing through a fiber optic bronchoscope. In some cases, medical providers may find that correct positioning can be accomplished without direct vision. The blocker tip 130 may be steered to the correct bronchus using, for example, one or more techniques or apparatus described above. The position of the bronchial blocker 120 is fixed and secured with respect to the endotracheal tube 112, in that the bronchial blocker 120 is physically coupled to the endotracheal tube 112. The security of the positioning of the endotracheal tube 112 in the trachea 102 is improved once the second inflatable element 132 is inflated in position. In the event that the bronchial blocker 120 becomes dislodged at some point (due to positioning of the patient, for example, or during surgery) the inflatable elements 122 and 132 may be readily deflated, and the apparatus 110 correctly repositioned, and the inflatable elements 122 and 132 readily re-inflated.

Materials used to construct the apparatus may be conventional. Tubes may be formed from, for example, polyvinyl chloride or natural or synthetic rubber, or rubber-like materials. The tubes may include additional structural features such as wire reinforcement or radio opaque materials.

Figure 3D:
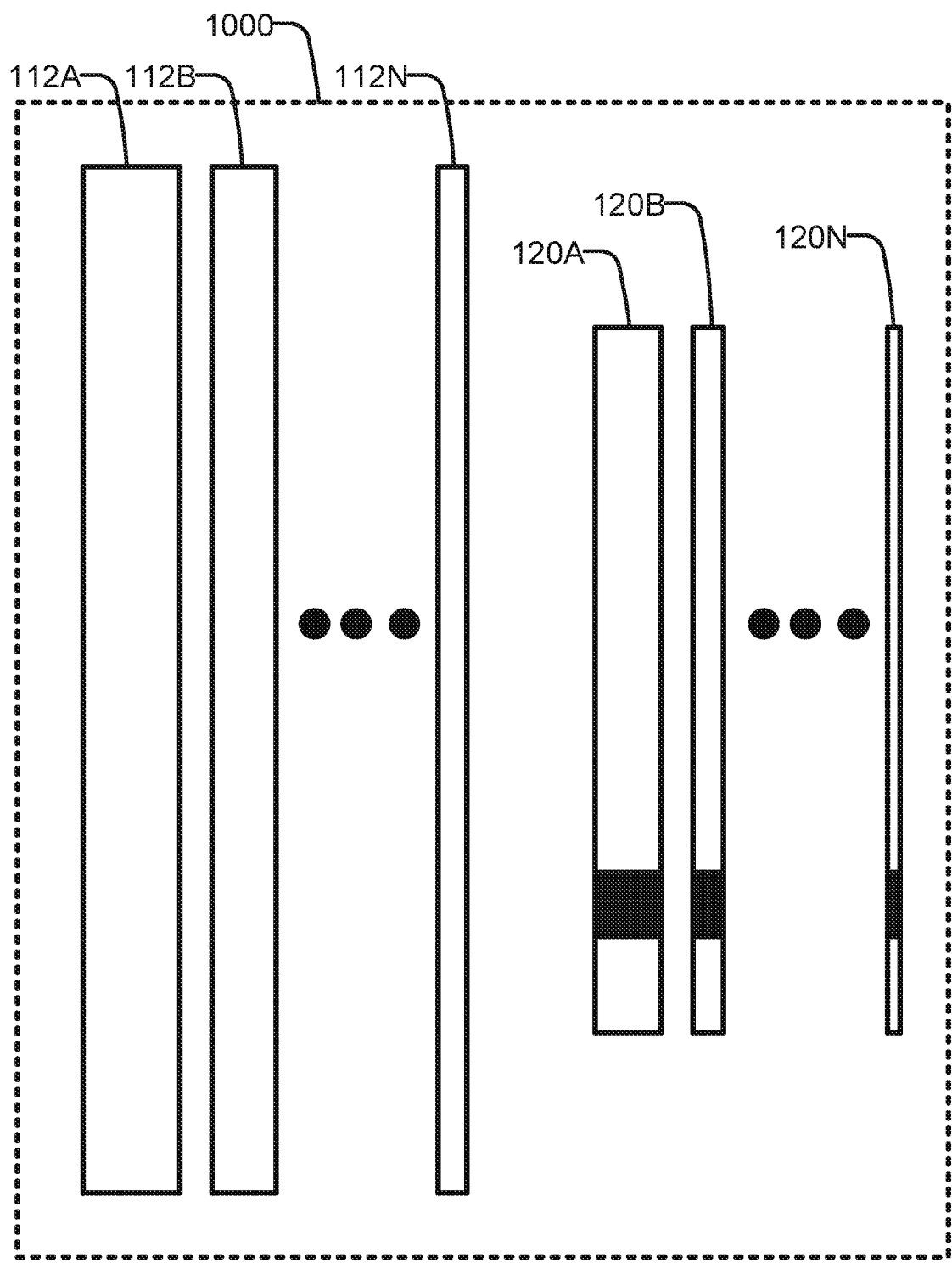
FIG. 3D is a schematic view of an illustrative kit comprising a plurality of endotracheal tubes and a plurality of bronchial blockers.

The concept can be embodied as a "kit," that is, as a collection of components that can be assembled to the needs of a particular patient. An apparatus 110 may be assembled quickly for a patient from such a kit, taking into account factors such as the patient's size and the lung that needs to be blocked (or other need, such as addressing a TEF). FIG. 3D is a schematic view of a kit 1000 according to an example embodiment. Kit 1000 may include one or more endotracheal tubes 112A, 112B, . . . , 112N of different sizes or configurations, and one or more bronchial blockers 120A, 120B, . . . , 120N of different sizes or configurations. Kit 1000 may include one or more steering balloon apparatus of different sizes or configurations. In a variation, some of the endotracheal tubes 112A, 112B, . . . , 112N may include the apparatus associated with the steering balloon apparatus (e.g., with the endotracheal tube and steering balloon apparatus already physically coupled), and some may not. In another variation, some of the bronchial blockers 120A, 120B, . . . , 120N may include the apparatus associated with the steering balloon apparatus, and some may not. By selection of components of desired sizes and configurations, and by physically coupling the components together, an apparatus best suited for the patient (e.g., whether large or small, blocking the right side or the left) may be readily selected, assembled and employed.

Figure 4:
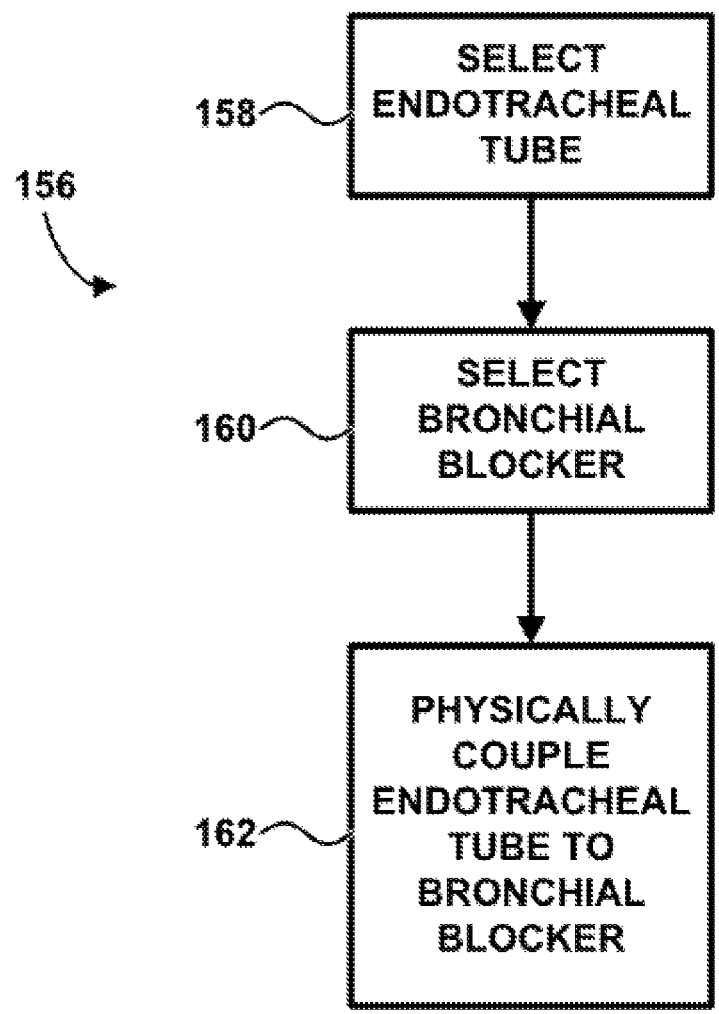
FIG. 4 is a flow diagram illustrating a method for preparation of a medical apparatus.

FIG. 4 illustrates an assembly process (156) for use with such a kit. From a plurality of endotracheal tubes of variant sizes and configurations, a particular endotracheal tube is selected (158). From a plurality of bronchial blockers, a particular bronchial blocker is selected (160). The selection of endotracheal tube and bronchial blocker may depend upon, for example, the age of the patient, the size of the patient, the medical objective to be achieved (such as lung isolation), which bronchus is to be occluded, the capability of the selected endotracheal tube and the selected bronchial blocker to work together, and so on. The bronchial blocker may be selected (160) before the endotracheal tube is selected (158). Once the endotracheal tube and the bronchial blocker are selected, the selected endotracheal tube may be physically coupled to the selected bronchial blocker (162). The endotracheal tubes and the bronchial blockers may be configured to be capable of physical coupling to one another with an attachment structure, such as grooves or adhesive. In an illustrative kit, many (not all) of the endotracheal tubes in the plurality of endotracheal tubes may be capable of physical coupling to many (if not to all) of the bronchial blockers in the plurality of bronchial blockers, as these components are generally configured to be capable of physical coupling to one another with one or more attachment structures. Once physical coupling is performed, the assembled apparatus may be put to use.

Assembly may be performed by the anesthesiologist, for example, or one operating under the direction of the anesthesiologist. A typical usage of the assembled apparatus for lung isolation may be a follows: the patient is anesthetized; the patient is intubated; the patient is stabilized and the position of the endotracheal tube is confirmed; a fiber optic bronchoscope is inserted into the endotracheal tube; the tip of the bronchial blocker is steered to the correct bronchus using one or more of the techniques described above; the blocker is inflated and its placement confirmed; the endotracheal tube is secured to the patient; the patient is positioned; the position of the blocker is re-checked; and the surgery proceeds. Numerous other scenarios are possible and are contemplated, but in this typical scenario, many benefits of the assembled apparatus may be realized in the ease of steering, the time used to place the blocker, and the readiness with which the assembled apparatus can be checked and re-positioned if desired.

Figure 5:
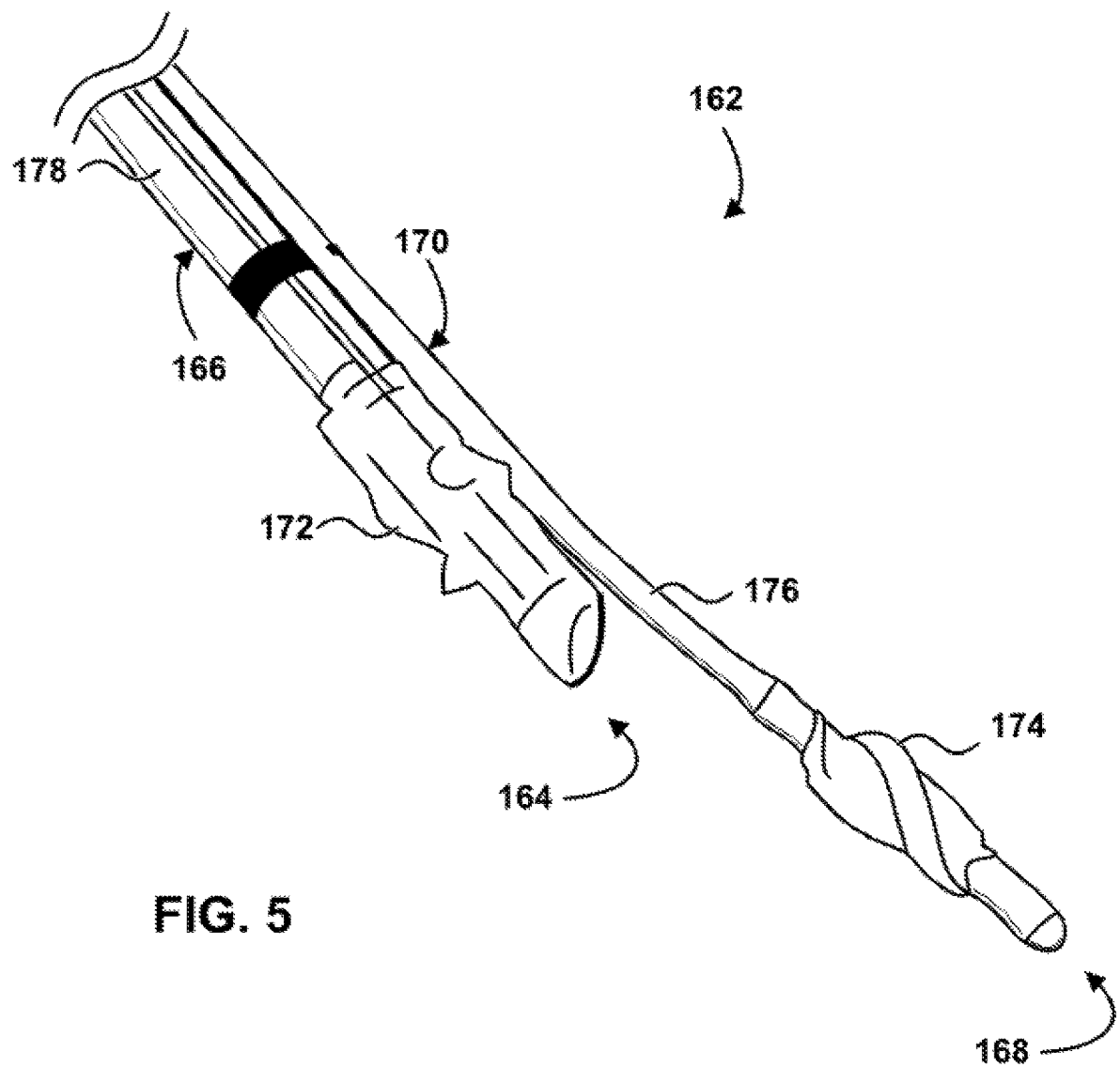
FIG. 5 is a plan view of a distal end of an illustrative endotracheal tube and tube of a bronchial blocker that have been physically coupled.

FIG. 5 shows a portion of an illustrative medical apparatus 164. This apparatus 164 is sized for a neonate or an infant (aged from day of birth to six months of age). Further, this apparatus was constructed and was used for testing and evaluation of the effectiveness and prospective advantages of some of the subject matter claimed below.

A distal end 166 of an endotracheal tube 168 is depicted, along with a distal end 170 of a bronchial blocker 172. The entirely of the apparatus 164 is not shown in FIG. 5.

The endotracheal tube 168 includes a cuff-like first inflatable element 174, shown in FIG. 5 as deflated. The first inflatable element 174 is optional; for very small patients, such as premature babies, a cuff (or other inflatable element) may be omitted. The smallest conventional cuffed endotracheal tube may have an internal diameter of about 3.0 mm, which may be too large for a premature baby. For very small premature babies, an uncuffed 2.0 mm or 2.5 mm diameter endotracheal tube may be used. For inclusion in a kit as described above, endotracheal tubes may be available in 2.0 and/or 2.5 mm sizes, among others. Such small tubes may also be available in cuffed and uncuffed varieties.

In FIG. 5, the first inflatable element 174 may be inflated and deflated by way of a first inflation lumen in a first inflation tube (not explicitly shown), included with the endotracheal tube 168. The bronchial blocker 172 includes a balloon-type second inflatable element 176, shown in FIG. 5 as deflated. The second inflatable element 176 is inflated and deflated by way of a second inflation lumen in a second inflation tube 178.

The endotracheal tube 168 is physically coupled to the bronchial blocker 172, such that the apparatus 164 can be inserted into the patient as a single unit. Sliding the endotracheal tube 168 into the patient's trachea also slides the bronchial blocker 172, and vice versa. In the apparatus 164, the endotracheal tube 168 is physically coupled to the bronchial blocker 172 by a bio-compatible adhesive (not explicitly shown), which operates as an attachment structure. The endotracheal tube 168 and the bronchial blocker 172, particularly the second inflation lumen in a second inflation tube 178, are physically coupled side-by-side. The second inflation tube 178 of the bronchial blocker 172 is not inside the lumen 180 of the endotracheal tube 168; in other words, the tubes are non-concentric, and the second inflation tube 178 is side-by-side with the endotracheal tube 168.

The embodiment of the apparatus 164 omits a third inflatable element that may be used to steer the distal end 170 of the bronchial blocker 172. It has been indicated by experimentation that the distal end 170 of the bronchial blocker 172 may be steered into the correct bronchus of a very young patient without a third inflatable element. When the apparatus 164 is introduced into the trachea of a very young patient, the first inflatable element 174 and the second inflatable element 176 are deflated. The endotracheal tube 168 and the bronchial blocker 172 are physically coupled side-by-side, which may serve to bias the distal end 170 of the bronchial blocker 164 in a desired direction. When inserted into the trachea, the distal end 170 of the bronchial blocker 164 may tend toward the left mainstem bronchus of the patient, for example. If the left bronchus is to be occluded, such biasing may be helpful in steering the distal end 170 where it ought to go. If additional steering may be helpful, the first inflatable element 174 may be gently, but generally not fully, inflated when the distal end 170 of the bronchial blocker 172 reaches the mainstem bronchi. Such gentle inflation avoids holding the endotracheal tube 168 in place in the trachea. If the distal end 170 of the bronchial blocker 172 is biased to the left, for example, inflation of the first inflatable element 174 may urge the distal end 170 of the bronchial blocker 172 further to the left, and into the correct bronchus. The first inflatable element 174 may be deflated, the endotracheal tube 168 and bronchial blocker 172 may be positioned, the first inflatable element 174 may be re-inflated, and the second inflatable element 176 may be inflated to occlude the correct mainstem bronchus.

Figure 6:
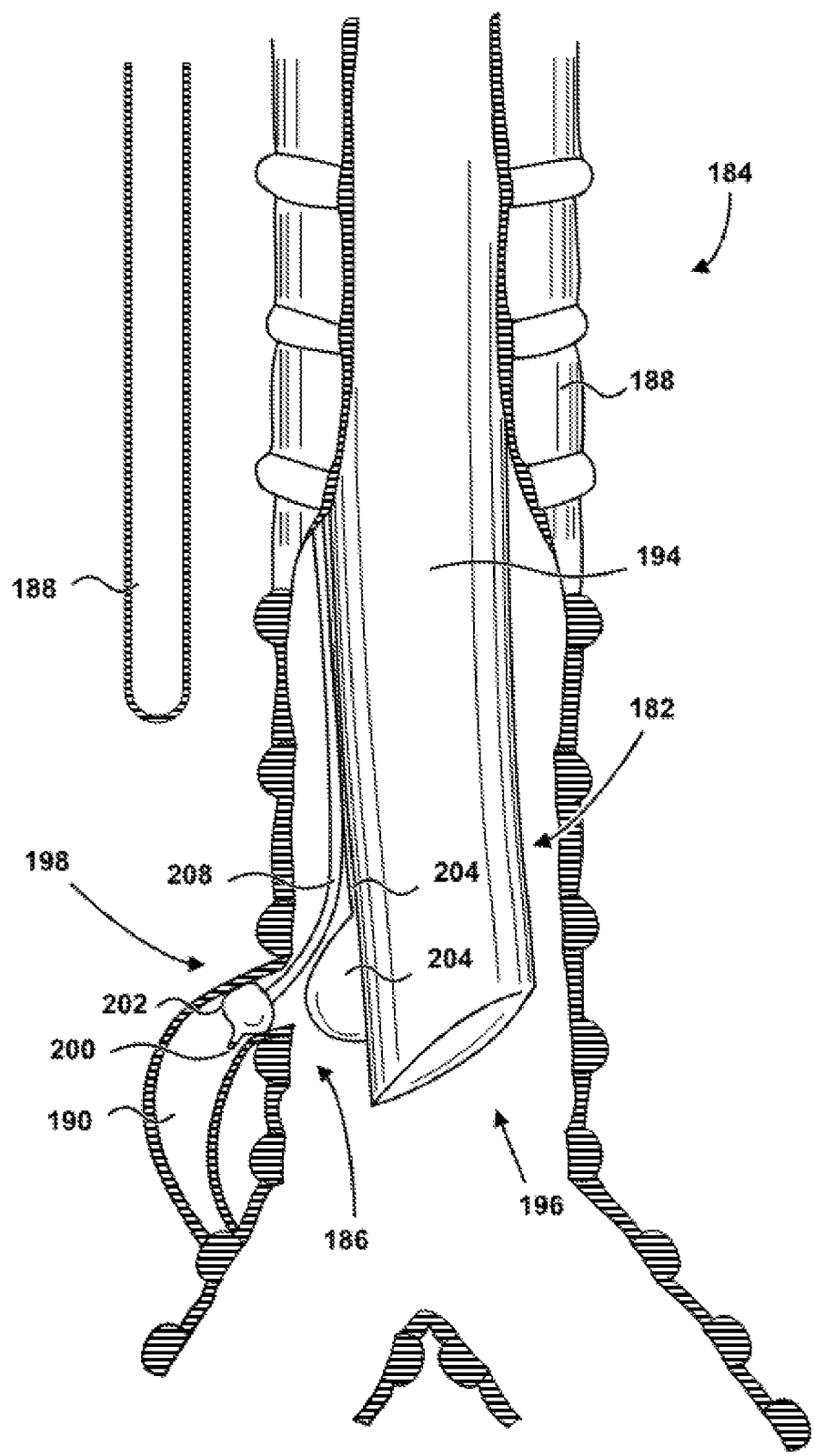
FIG. 6 is a schematic view of another illustrative medical device used with the respiratory and digestive systems of a newborn patient.

FIG. 6 shows a portion of an illustrative medical apparatus 182 in an illustrative use with part of the respiratory and digestive systems 184 of a neonate, that is, a newborn patient. The patient is depicted as having a TEF 186, in which an opening has formed between the trachea 188 and a segment of esophagus 190 leading to the stomach (not shown in FIG. 6). The patient is further depicted as having proximal esophageal atresia, in which the upper or proximal end of the esophagus 192 terminates and does not connect with the lower esophagus 190. There are many variations of esophageal atresia (Gross of Boston, for example, identifies five classifications); FIG. 6 depicts one of those variations, but the apparatus and techniques may be applied to other variations as well, as well as to other variations of fistulas. It may also be noted that the trachea 188 and upper esophagus 190 are depicted in FIG. 6 as separated from one another side-by-side; in an actual patient, these structures may be physically closer to each other and one may be behind the other.

The apparatus 182 includes an endotracheal tube 194, of which the distal end 196 is shown in FIG. 6. The endotracheal tube 194 shown in FIG. 6 need not have the same inner diameter as the endotracheal tube 112 shown in FIG. 1 (and may have an inner diameter smaller than the endotracheal tube 112 shown in FIG. 1); and the trachea 188 of the neonate may be considerably smaller than the trachea 102 shown in FIG. 1. The endotracheal tube 194 is uncuffed, that is, the endotracheal tube 194 lacks an inflatable element comparable to cuff 122 shown in FIG. 1.

A balloon catheter 198 (similar in some respects to the bronchial blocker 120 shown in FIG. 1, but smaller and possibly having structural differences that are not pertinent here) has been physically coupled to the endotracheal tube 194. As shown in FIG. 6, the distal end 200 of the balloon catheter 198 has been directed into the TEF 186, and the balloon 202 of the balloon catheter 198 has been inflated through a catheter tube 204. The inflated balloon 202 is blocking the fistula 186. This blocking of the passage to the stomach may serve to prevent inflation of the stomach when applying positive pressure ventilation to the lungs during surgery; the blocking may also serve to prevent any passage of any substance from the digestive system to the respiratory system, or vice versa. Surgery may be performed shortly after birth to close the fistula 186 and repair the esophagus.

Blocking the fistula 186 can be a delicate procedure, and moving the distal end 200 of the balloon catheter 198 into the TEF 186 can be challenging. As depicted in FIG. 6, the lower end of the esophagus 190 branches laterally away from the trachea 188 in this patient. A steering balloon 206, inflated through a tube 208, is depicted in FIG. 6 as directing or deflecting the distal end 200 of the balloon catheter 198 into the TEF 186. The steering balloon 206 and/or tube 208 may be physically coupled to the endotracheal tube 194 by an attachment structure such as those described previously. The steering balloon 206 can deflect the distal end 200 of the balloon catheter 198 laterally, thereby supporting ready introduction of the distal end 200 of the balloon catheter 198 into the TEF 186. Although FIG. 6 depicts the catheter balloon 202 and the steering balloon 206 inflated at the same time, it may also be decided to deflate the steering balloon 206 before inflating the catheter balloon 202; the balloons 202 and 206 are generally independently inflatable elements.

As already mentioned, inflation and deflation of the steering balloon 206 may be performed in concert with one or more other steering techniques or apparatus, which may assist with directing the balloon catheter 198 to a desired position.

As noted above, the apparatus and techniques may be applied to different variations of esophageal atresias and fistulas. The steering balloon 206 may be used to steer apparatus other than a balloon catheter 198. For example, there may be a situation in which it may be desired to introduce a wire through a fistula into the patient's esophagus. The steering balloon 206 physically coupled to the endothracheal tube 194 may be inflated to direct a distal end of the wire through the fistula into the esophagus. The steered apparatus may be, but need not be, physically coupled to the endotracheal tube 194.

The disclosed apparatus and techniques for assembly and use thereof may realize one or more potential advantages, many of which were discovered or verified by clinical testing. Some of the potential benefits or differences have been mentioned already. The disclosed apparatus and techniques have been found by experimentation to produce effects distinct from other apparatus and techniques.

For example, in patients less than six years of age, some medical providers have accomplished lung isolation by placing an endotracheal tube, and separately placing an bronchial blocker. The separate placement of the bronchial blocker, if deployed through the lumen of the endotracheal tube, is often time consuming and requires significant dexterity and expertise. When the blocker tip emerges from the distal end of the endotracheal tube, it may be challenging to steer the blocker tip to the correct bronchus. Further, it has been observed that if the bronchial blocker is dislodged during positioning or surgery, re-positioning the bronchial blocker may be difficult and time-consuming, possibly delaying surgery and placing the patient at risk of complete airway obstruction. Some pediatric anesthesiologists may place the blocker "blind" (without direct vision such as with the use of a fiber optic bronchoscope), and check positioning after placement. "Blind" placement may simplify insertion, but it may also carry a risk of a need for re-positioning.

It has been discovered by experimentation that the disclosed apparatus 110 (and 164 and 182) can be placed more quickly and readily, especially in a pediatric patient. The physical coupling of components supports placement of the endotracheal tube 112 (and 168) and the bronchial blocker 120 (and 172) at about the same time. Various physical features support steering the bronchial blocker 120 (and 172) to the correct bronchus, possibly without need for direct vision. Further, if the bronchial blocker 120 (and 172) is dislodged during positioning or surgery, re-positioning is less difficult and time-consuming.

Due to the ease of insertion and rapidity of securing the bronchial blocker 120 (and 172) in the correct bronchus, there is reduced incidence of desaturation and hypoxic events, especially in infants and neonates. Thus the airway can be secured after induction of anesthesia, the patient ventilated and optimized, and then the bronchial blocker 120 (and 172) advanced into the bronchus in a controlled and stable setting.

A further potential advantage may be ready and rapid customization of device sizes and features. Customization may be especially advantageous for pediatric patients, in that components of appropriate size may be selected, and may be assembled to make proper placement easier. Once an endotracheal tube and the bronchial blocker (for example) are selected, they can quickly and readily be physically coupled together in a manner that may be advantageous to the patient, such as by biasing the device to the right or left bronchus. Many commercially available devices are left-biased, and fewer are right-biased. The concept described herein can help avoid the situation in which there is a shortage of right-biased devices, because some embodiments support left- and right-biasing on short notice.

Once the endotracheal tube and the bronchial blocker are physically connected, the assembled apparatus may be easily and rapidly inserted.

Customization enables not only the use of smaller components, but also the use of larger ones. An endotracheal may be selected, for example, that has a lumen with a larger internal diameter than may be presently available in double-lumen tubes. Selecting a tube with a larger lumen may be an advantage when, for example, there are increased risks of the lumen becoming obstructed with secretions or blood clots, or use of a larger fiber optic bronchoscope is indicated, or more room for suction is indicated, or having less resistance during ventilation is indicated. Further, an endotracheal tube may be selected for positioning and/or manipulating other diagnostic and therapeutic medical devices, such as (but not limited to) flexible biopsy forceps, flexible cautery cable, lasers, catheters, suction catheters, brushes, and other medical instruments. An endotracheal tube may be selected based upon a combination of factors as well as the size of the patient. For example, an endotracheal tube may be selected to accommodate a flexible basket and grasping forceps for removal of foreign bodies in the airway; airway foreign bodies being an unfortunately common medical problem in small children.

The embodiments described above are intended to be examples only. Alterations, modifications and variations can be effected to the particular embodiments without departing from the scope of the concept, which is defined by the claims appended hereto.

The invention claimed is:

1. An apparatus comprising:
an endotracheal tube having a proximal end and a distal end; and
a bronchial blocker having a proximal end and a distal end, the distal end of the bronchial blocker including an inflatable element receivable within a bronchus of a lung, the inflatable element inflatable to substantially occlude the bronchus within which the inflatable element is received to prevent flow of fluid into or out of the lung;
wherein the endotracheal tube and the bronchial blocker as non-unitary elements are detachably physically coupled to one another by a first attachment structure near the distal end of the endotracheal tube to form a single unit wherein the bronchial blocker and the endotracheal tube are side-by-side and non-concentric; and
wherein the distal end of the bronchial blocker extends beyond the distal end of the endotracheal tube.

2. The apparatus of claim 1,
wherein the bronchial blocker includes an inflation tube;
wherein the endotracheal tube comprises a right side and a left side;
wherein the endotracheal tube comprises the first attachment structure disposed on the right side of the endotracheal tube and a second attachment structure disposed on the left side of the endotracheal tube; and
wherein the first attachment structure and the second attachment structure are sized to receive the inflation tube of the bronchial blocker.

3. The apparatus of claim 2, wherein the first attachment structure comprises a groove and the second attachment structure comprises a groove.

4. The apparatus of claim 1, wherein the first attachment structure comprises a bio-compatible adhesive.

5. The apparatus of claim 4, wherein the first attachment structure comprises an adhesive strip, and wherein the adhesive strip comprises the bio-compatible adhesive.

6. The apparatus of claim 1, wherein the endotracheal tube comprises:
a third inflatable element disposed near the distal end of the endotracheal tube; and
a third inflation tube in fluid communication with the third inflatable element;
wherein inflating the third inflatable element deflects the inflatable element of the bronchial blocker laterally relative to the distal end of the endotracheal tube.

7. The apparatus of claim 6, further comprising:
a bulb in fluid communication with the third inflation tube and the third inflatable element.

8. The apparatus of claim 1 wherein the bronchial blocker is detachably physically coupled to the endotracheal tube to move together longitudinally with the endotracheal tube.

9. The apparatus of claim 8 wherein the bronchial blocker comprises an inflation tube coupling the inflatable element of the bronchial blocker to the endotracheal tube, the inflatable element suspended from the inflation tube such that the inflatable element is movable laterally relative to the distal end of the endotracheal tube.

10. The apparatus of claim 1, wherein the endotracheal tube comprises:
a first inflatable element disposed near the distal end of the endotracheal tube; and
a first inflation tube in fluid communication with the first inflatable element;
wherein the first inflatable element comprises a circumferential inflatable cuff.

11. The apparatus of claim 1, wherein the bronchial blocker comprises:
a second inflation tube in fluid communication with the inflatable element of the bronchial blocker.

12. The apparatus of claim 1, wherein the endotracheal tube comprises an endotracheal tube lumen having an internal diameter, and wherein the internal diameter is in the range of 2.0 mm to 9.0 mm.

13. The apparatus of claim 1,
wherein the bronchial blocker includes an inflation tube, and
wherein the inflation tube of the bronchial blocker and the endotracheal tube are side-by-side.

14. The apparatus of claim 1 wherein the bronchial blocker is detachably physically coupled to the endotracheal tube to rotate with the endotracheal tube.

15. The apparatus of claim 1 wherein the endotracheal tube and the bronchial blocker are detachably physically coupled to one another by an additional attachment structure located near a midpoint between the distal end and the proximal end of the endotracheal tube.

16. A kit comprising:
a plurality of endotracheal tubes of variant sizes and configurations, each of the plurality of endotracheal tubes having a proximal end and a distal end; and
a plurality of bronchial blockers of variant sizes and configurations, each of the plurality of bronchial blockers having a proximal and a distal end, the distal end of each of the plurality of bronchial blockers including an inflatable element receivable within a bronchus of a lung, the inflatable element inflatable to substantially occlude the bronchus within which the inflatable element is received to prevent flow of fluid into or out of the lung;
wherein any of the endotracheal tubes in the plurality of endotracheal tubes is configured to be capable of physical coupling to any of the bronchial blockers in the plurality of bronchial blockers, with an attachment structure to form a single unit wherein when any selected one of the endotracheal tubes is physically coupled to any selected one of the bronchial blockers, the selected endotracheal tube and the selected bronchial blocker are side-by-side and non-concentric and the distal end of the selected bronchial blocker extends beyond the distal end of the selected endotracheal tube.

17. The kit of claim 16, wherein at least one of the endotracheal tubes in the plurality of endotracheal tubes includes an endotracheal tube lumen having a first internal diameter, and another of the endotracheal tubes in the plurality of endotracheal tubes includes an endotracheal tube lumen having a second internal diameter.

18. The kit of claim 17, wherein the first internal diameter and the second internal diameter are in a range of 2.0 mm to 9.0 mm.

19. The kit of claim 16, further comprising:
a plurality of steering balloon apparatus of variant sizes and configurations;
wherein any of the endotracheal tubes in the plurality of endotracheal tubes is configured to be capable of physical coupling to any of the steering balloon apparatus in the plurality of steering balloon apparatus, with the attachment structure.

* * * * *